(12) United States Patent
Wang et al.

(10) Patent No.: US 12,384,006 B2
(45) Date of Patent: Aug. 12, 2025

(54) SURGICAL DEVICE HAVING CHANGEABLE ELEMENTS

(71) Applicant: GYRUS ACMI, INC., Southborough, MA (US)

(72) Inventors: Huisun Wang, Maple Grove, MN (US); Kester Julian Batchelor, Mound, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 1241 days.

(21) Appl. No.: 16/919,233

(22) Filed: Jul. 2, 2020

(65) Prior Publication Data
US 2020/0330151 A1    Oct. 22, 2020

Related U.S. Application Data

(62) Division of application No. 15/817,707, filed on Nov. 20, 2017, now Pat. No. 10,702,331, which is a
(Continued)

(51) Int. Cl.
| | | |
|---|---|---|
| B25B 7/00 | (2006.01) | |
| A61B 17/00 | (2006.01) | |

(Continued)

(52) U.S. Cl.
CPC ............... B25B 7/00 (2013.01); A61B 17/29 (2013.01); A61B 18/1442 (2013.01);
(Continued)

(58) Field of Classification Search
CPC ........ A61B 17/28–295; A61B 18/1442; A61B 17/30; A61B 17/128; B25B 7/04; B25B 9/02; B25B 7/00
(Continued)

(56) References Cited

U.S. PATENT DOCUMENTS

| | | |
|---|---|---|
| 2,010,493 A | 8/1935 | La |
| 2,109,147 A | 2/1938 | Grosso |

(Continued)

FOREIGN PATENT DOCUMENTS

| | | |
|---|---|---|
| CN | 101277654 A | 10/2008 |
| CN | 203042442 U | 7/2013 |

(Continued)

OTHER PUBLICATIONS

U.S. Appl. No. 14/595,484 U.S. Pat. No. 9,855,091, filed Jan. 13, 2015, Surgical Device Having Changeable Elements.
(Continued)

*Primary Examiner* — Kathleen S Holwerda
*Assistant Examiner* — Serenity A Miller
(74) *Attorney, Agent, or Firm* — Schwegman Lundberg & Woessner, P.A.

(57) ABSTRACT

An electrosurgical device kit includes an elongate first member, an elongate second member disposed adjacent to the first member, the second member being at least movably coupled to the first member, a first electrode head removably attachable to the first member, a second electrode head removably attachable to the first member, and a third electrode head coupled to the second member. The first, second, and third electrode heads are configured to apply a current to a tissue, the first and second electrode heads being non-identical.

16 Claims, 7 Drawing Sheets

Related U.S. Application Data division of application No. 14/595,484, filed on Jan. 13, 2015, now Pat. No. 9,855,091.

(60) Provisional application No. 61/974,407, filed on Apr. 2, 2014.

(51) Int. Cl.
  *A61B 17/29* (2006.01)
  *A61B 18/00* (2006.01)
  *A61B 18/14* (2006.01)
  *B25B 7/04* (2006.01)
  *B25B 9/02* (2006.01)

(52) U.S. Cl.
  CPC ............ *A61B 18/1445* (2013.01); *B25B 7/04* (2013.01); *B25B 9/02* (2013.01); *A61B 2017/00473* (2013.01); *A61B 2017/2929* (2013.01); *A61B 2017/2943* (2013.01); *A61B 2018/00107* (2013.01); *A61B 2018/00589* (2013.01); *A61B 2018/0063* (2013.01); *A61B 2018/1452* (2013.01); *A61B 2018/1462* (2013.01); *A61B 2018/1495* (2013.01)

(58) Field of Classification Search
  USPC .................. 606/205, 206, 207; 294/99.2
  See application file for complete search history.

(56) References Cited

U.S. PATENT DOCUMENTS

| | | | |
|---|---|---|---|
| 2,406,393 | A | 8/1946 | Neugass |
| 3,044,081 | A | 7/1962 | Robinson, Jr. |
| 3,484,924 | A | 12/1969 | Dahl |
| 3,818,784 | A | 6/1974 | McClure |
| 4,074,718 | A | 2/1978 | Morrison, Jr. |
| 4,389,912 | A | 6/1983 | Dallons et al. |
| 4,478,221 | A | 10/1984 | Heiss |
| 4,634,165 | A | 1/1987 | Russell. et al. |
| 4,657,016 | A | 4/1987 | Ellman et al. |
| 4,903,696 | A | 2/1990 | Stasz et al. |
| 5,047,046 | A | 9/1991 | Bodoia |
| 5,057,016 | A | 10/1991 | Lukase et al. |
| 5,190,335 | A | 3/1993 | Rommerdale |
| 5,334,215 | A | 8/1994 | Chen |
| 5,342,381 | A | 8/1994 | Tidemand |
| 5,445,638 | A | 8/1995 | Rydell et al. |
| 5,462,546 | A | 10/1995 | Rydell |
| 5,496,317 | A | 3/1996 | Goble et al. |
| 5,542,167 | A | 8/1996 | Nakamoto |
| 5,649,938 | A * | 7/1997 | Allen .................. A61B 17/1114 606/151 |
| 5,797,959 | A | 8/1998 | Castro et al. |
| 5,810,805 | A | 9/1998 | Sutcu et al. |
| 5,899,513 | A | 5/1999 | Grisoni |
| 5,902,301 | A | 5/1999 | Olig |
| 6,007,552 | A * | 12/1999 | Fogarty ................. A61B 17/122 606/157 |
| 6,050,996 | A | 4/2000 | Schmaltz et al. |
| 6,096,037 | A | 8/2000 | Mulier et al. |
| 6,099,539 | A * | 8/2000 | Howell ................ A61B 17/122 606/151 |
| 6,110,171 | A | 8/2000 | Rydell |
| 6,152,924 | A | 11/2000 | Parins |
| 6,174,309 | B1 | 1/2001 | Wrublewski et al. |
| 6,190,386 | B1 | 2/2001 | Rydell |
| 6,257,105 | B1 * | 7/2001 | Lin ....................... B25B 27/205 29/229 |
| 6,293,954 | B1 | 9/2001 | Fogarty et al. |
| 6,786,117 | B1 | 9/2004 | Tseng |
| 7,229,111 | B2 | 6/2007 | Cohen et al. |
| 7,235,073 | B2 | 6/2007 | Levine et al. |
| 7,641,248 | B2 | 1/2010 | Cho |
| 7,931,668 | B2 | 4/2011 | Sloat |
| 7,938,469 | B2 | 5/2011 | Ait-mani |
| 7,938,779 | B2 | 5/2011 | Sakurai et al. |
| 8,048,107 | B2 | 11/2011 | Chen |
| 8,152,212 | B2 | 4/2012 | Sugiyama |
| 9,452,011 | B2 | 9/2016 | Batchelor et al. |
| 9,855,091 | B2 | 1/2018 | Wang et al. |
| 10,702,331 | B2 | 7/2020 | Wang et al. |
| 11,266,407 | B2 * | 3/2022 | Bagley .............. A61B 17/1285 |
| 2002/0023524 | A1 * | 2/2002 | Lowe ...................... B25F 1/003 81/427.5 |
| 2003/0181904 | A1 | 9/2003 | Levine et al. |
| 2004/0158241 | A1 | 8/2004 | Battles et al. |
| 2005/0021025 | A1 | 1/2005 | Buysse et al. |
| 2005/0119650 | A1 | 6/2005 | Sanders et al. |
| 2006/0047278 | A1 | 3/2006 | Christian et al. |
| 2006/0271042 | A1 | 11/2006 | Latterell et al. |
| 2007/0244480 | A1 | 10/2007 | Suzuki |
| 2008/0065021 | A1 | 3/2008 | Jenkins et al. |
| 2010/0035564 | A1 | 2/2010 | Lee |
| 2010/0057084 | A1 * | 3/2010 | Hanna ................ A61B 18/1445 606/51 |
| 2010/0145335 | A1 | 6/2010 | Johnson et al. |
| 2010/0198248 | A1 | 8/2010 | Vakharia |
| 2011/0071519 | A1 | 3/2011 | Rothstein et al. |
| 2011/0087219 | A1 | 4/2011 | Batross et al. |
| 2012/0059375 | A1 | 3/2012 | Couture et al. |
| 2012/0296172 | A1 * | 11/2012 | Raven, III ......... A61B 17/0206 600/231 |
| 2013/0116682 | A1 | 5/2013 | Koo et al. |
| 2013/0197516 | A1 * | 8/2013 | Kappel .................. A61B 17/29 606/46 |
| 2013/0226200 | A1 * | 8/2013 | Kappel ................ A61B 17/128 606/142 |
| 2013/0253489 | A1 | 9/2013 | Nau, Jr. et al. |
| 2013/0274740 | A1 | 10/2013 | Dickson et al. |
| 2014/0094801 | A1 | 4/2014 | Boudreaux et al. |
| 2015/0282871 | A1 | 10/2015 | Wang et al. |
| 2018/0071013 | A1 | 3/2018 | Wang et al. |

FOREIGN PATENT DOCUMENTS

| | | |
|---|---|---|
| CN | 106535801 A | 3/2017 |
| CN | 106535801 B | 9/2020 |
| EP | 0904738 A2 | 3/1999 |
| EP | 1336384 A1 | 8/2003 |
| EP | 3110358 A1 | 1/2017 |
| EP | 3110358 B1 | 7/2023 |
| JP | S5167783 U | 5/1976 |
| JP | 05029444 A | 2/1993 |
| JP | 2004237105 A | 8/2004 |
| JP | 2009056291 A | 3/2009 |
| JP | 2010005464 A | 1/2010 |
| JP | 2012516716 A | 7/2012 |
| JP | 2017513574 A | 6/2017 |
| JP | 6333406 B2 | 5/2018 |
| JP | 2018138192 A | 9/2018 |
| JP | 6589007 B2 | 9/2019 |
| JP | 2020006213 A | 1/2020 |
| WO | WO-2005020834 A2 | 3/2005 |
| WO | WO-2015152979 A1 | 10/2016 |

OTHER PUBLICATIONS

U.S. Appl. No. 15/817,707 U.S. Pat. No. 10,702,331, filed Nov. 20, 2017, Surgical Device Having Changeable Elements.

"Japanese Application Serial No. 2019-166831, Notification of Reasons for Refusal mailed Aug. 21, 2020", w/ English translation, 6 pgs.

"Japanese Application Serial No. 2019-166831, Response filed Jan. 21, 2021 to Notification of Reasons for Refusal mailed Aug. 21, 2020", with English claims, 7 pgs.

"U.S. Appl. No. 14/595,484, Corrected Notice of Allowability mailed Nov. 21, 2017", 2 pgs.

"U.S. Appl. No. 14/595,484, Non Final Office Action mailed Jul. 6, 2017", 12 pgs.

"U.S. Appl. No. 14/595,484, Notice of Allowance mailed Oct. 12, 2017", 8 pgs.

(56) References Cited

OTHER PUBLICATIONS

"U.S. Appl. No. 14/595,484, Response filed Sep. 22, 2017 to Non Final Office Action mailed Jul. 6, 2017", 15 pgs.
"U.S. Appl. No. 15/817,707, Advisory Action mailed Jan. 31, 2020", 4 pgs.
"U.S. Appl. No. 15/817,707, Corrected Notice of Allowability mailed Apr. 20, 2020", 2 pgs.
"U.S. Appl. No. 15/817,707, Final Office Action mailed Oct. 21, 2019", 11 pgs.
"U.S. Appl. No. 15/817,707, Non Final Office Action mailed Jun. 26, 2019", 11 pgs.
"U.S. Appl. No. 15/817,707, Notice of Allowance mailed Mar. 2, 2020", 10 pgs.
"U.S. Appl. No. 15/817,707, Response filed Jan. 21, 2020 to Final Office Action mailed Oct. 21, 2019", 10 pgs.
"U.S. Appl. No. 15/817,707, Response filed Feb. 12, 2020 to Advisory Action mailed Jan. 31, 2020", 10 pgs.
"U.S. Appl. No. 15/817,707, Response filed Jun. 6, 2019 to Restriction Requirement mailed Apr. 23, 2019", 5 pgs.
"U.S. Appl. No. 15/817,707, Response filed Sep. 25, 2019 to Non Final Office Action mailed Jun. 26, 2019", 9 pgs.
"U.S. Appl. No. 15/817,707, Restriction Requirement mailed Apr. 23, 2019", 6 pgs.
"Chinese Application Serial No. 201680018044.X, Office Action mailed Mar. 15, 2019", W/English Translation, 13 pgs.
"Chinese Application Serial No. 201580018044.X, Office Action mailed Jul. 19, 2018", W/English Translation, 14 pgs.
"Chinese Application Serial No. 201580018044.X, Request for Reexamination filed Feb. 13, 2020", w/ English Claims, 18 pgs.
"International Application Serial No. PCT/US2015/011120, International Preliminary Report on Patentability mailed Oct. 13, 2016", 9 pgs.
"International Application Serial No. PCT/US2016/011120, International Search Report mailed Apr. 2, 2015", 4 pgs.
"International Application Serial No. PCT/US2015/011120, Written Opinion mailed Apr. 2, 2015", 7 pgs.
"Japanese Application Serial No. 2016-560413, Notice of Reasons for Refusal mailed Sep. 19, 2017", with English translation of claims, 8 pgs.
"Japanese Application Serial No. 2016-560413, Response filed Jan. 22, 2018 to Notice of Reasons for Refusal mailed Sep. 19, 2017", 11 pgs.
"Japanese Application Serial No. 2018-082839, Notice of Reasons for Refusal mailed Mar. 1, 2019", 14 pgs.
"Japanese Application Serial No. 2018-082839, Response filed Jun. 4, 2019 to Notice of Reasons for Refusal mailed Mar. 1, 2019", with English translation of claims, 13 pgs.
"European Application Serial No. 15703347.3, Response Filed Nov. 30, 2021 to Communication Pursuant to Article 94(3) EPC mailed May 25, 2021", 39 pgs.
"European Application Serial No. 15703347.3, Communication Pursuant to Article 94(3) EPC mailed May 25, 2021", 4 pgs.

\* cited by examiner

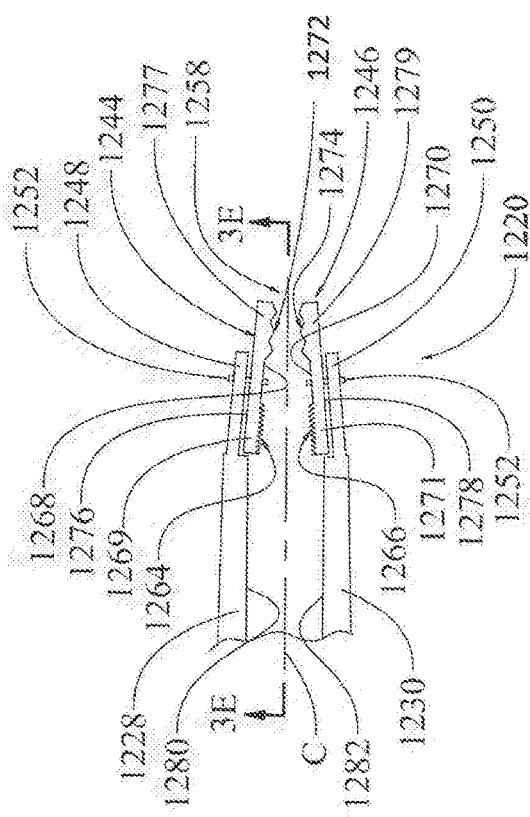
Fig. 3D
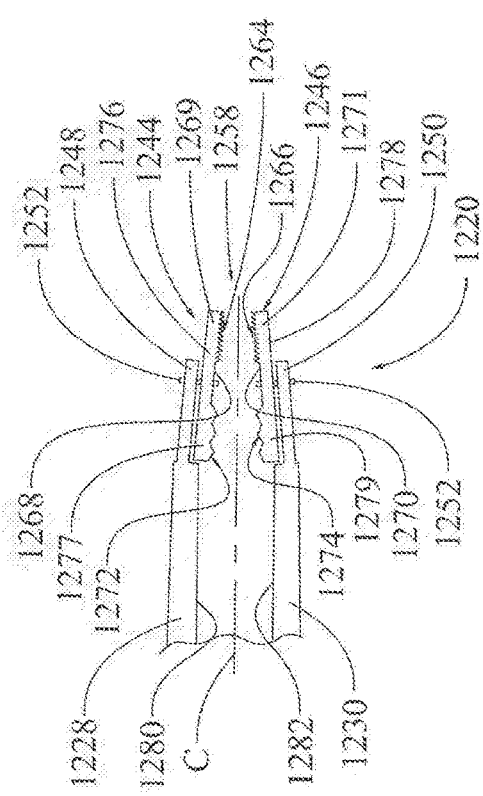
Fig. 3C
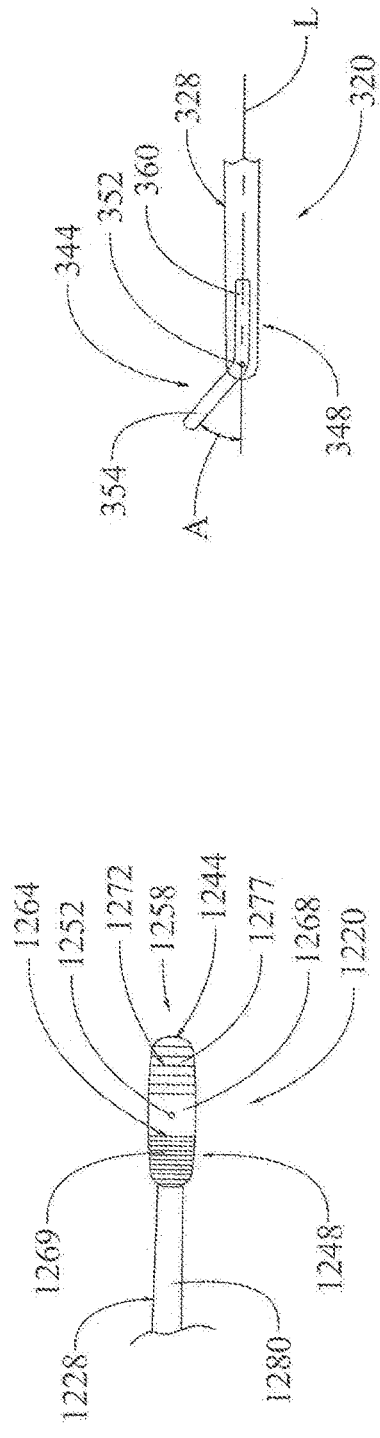
Fig. 4A
Fig. 3E

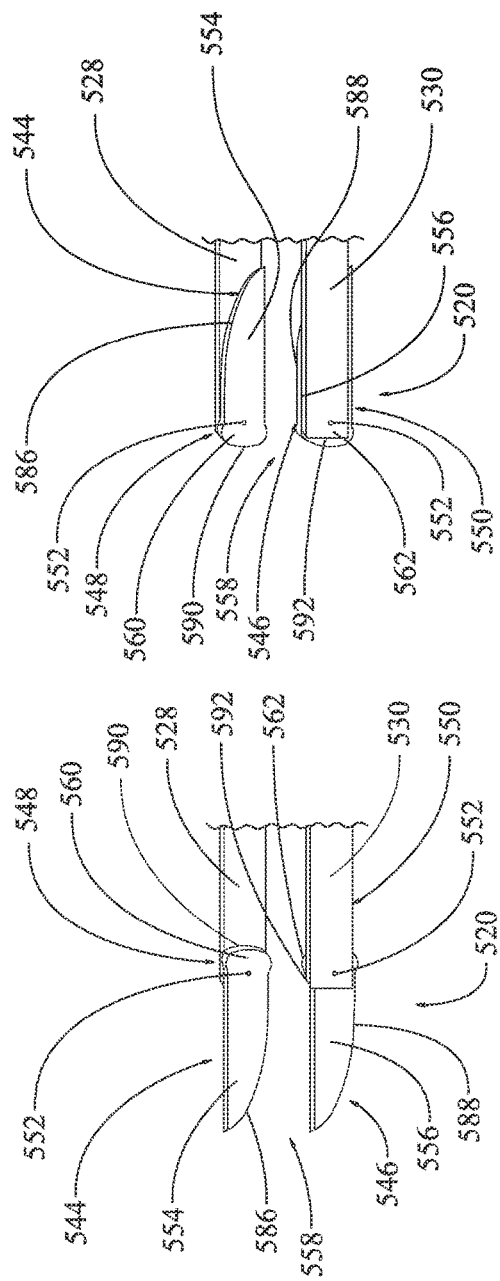
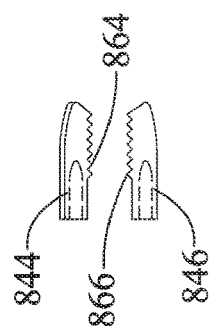
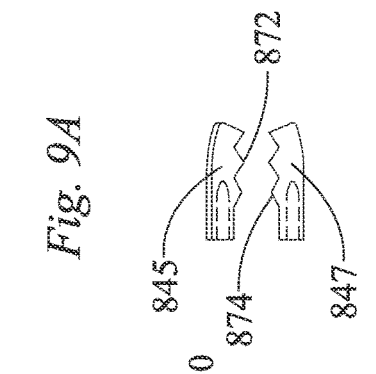
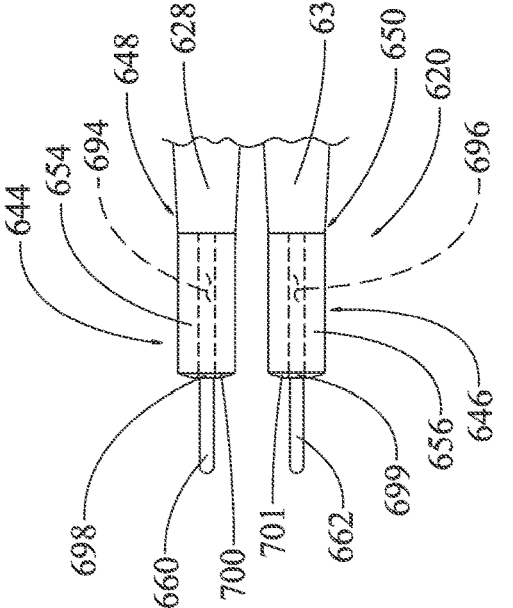
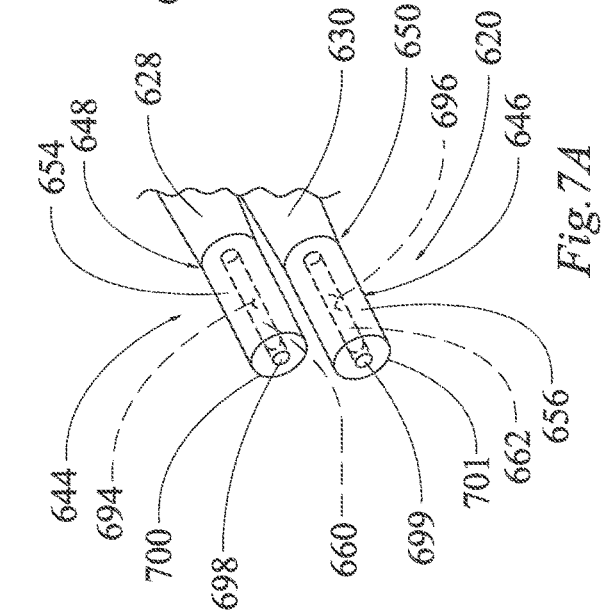

SURGICAL DEVICE HAVING CHANGEABLE ELEMENTS

RELATED APPLICATION

This application is a divisional of U.S. patent application Ser. No. 15/817,707, filed on Nov. 20, 2017, which is a divisional of U.S. application Ser. No. 14/595,484, filed on Jan. 13, 2015 and issued on Jan. 2, 2018 as U.S. Pat. No. 9,855,091, which claims the benefit of U.S. Provisional Patent Application No. 61/974,407, filed on Apr. 2, 2014.

The entire contents of the above applications are incorporated herein by reference in their entireties.

FIELD

The present disclosure relates to surgical devices, and more particular, surgical devices having opposed members that may be used for gripping or applying a current.

BACKGROUND

The statements in this section merely provide background information related to the present disclosure and may or may not constitute prior art.

Surgical forceps or tweezers are used in various applications during medical therapy procedures. Such devices are commonly used for holding or gripping objects.

Recently, medical practitioners have also used bipolar forceps and tweezers during surgical procedures. Bipolar forceps and tweezers may be used to seal vessels by delivering pulsed bipolar energy to coagulate nearby tissue, which may replace or minimize the need for sutures and staples.

Bipolar forceps and tweezers have a fixed size, and one device is used in a finite number of applications for which the device is properly sized. In addition, the devices have other fixed characteristics, which make them useful in only a limited number of applications. The same is true for regular, non-energized forceps and tweezers.

Accordingly, there is a need for more universally useful surgical devices, such as tweezers and forceps.

SUMMARY

The present disclosure provides a surgical device that has at least one end which may be changeable to fit the needs of various different or same procedures.

Accordingly, pursuant to one aspect of the invention, an electrosurgical device kit includes an elongate first member, an elongate second member disposed adjacent to the first member, the second member being at least movably coupled to the first member, a first electrode head removably attachable to the first member, a second electrode head removably attachable to the first member, and a third electrode head coupled to the second member. The first, second, and third electrode heads are configured to apply a current to a tissue, the first and second electrode heads being non-identical.

Accordingly, pursuant to another aspect of the invention, a device includes an elongate first member, an elongate second member disposed adjacent to the first member, the second member being at least movably coupled to the first member, and a forceps end coupled to the first member, at least a portion of the forceps end being movable with respect to the first member into a forceps end first position and a forceps end second position, the forceps end having a first portion and a second portion, the first portion having first set of teeth and the second portion having a second set of teeth.

The invention may be further characterized by one or any combination of the features described herein, such as: the first electrode is identical to the third electrode; the first electrode is sharper than the second electrode; the first electrode has a first coating disposed thereon and the second electrode has one of: no coating and a second coating disposed thereon, the first and second coatings being non-identical; the first electrode has a first electrode thermal capability and the second electrode has a second electrode thermal capability, the first electrode thermal capability being different than the second electrode thermal capability; the first electrode has a first electrode electrical capability and the second electrode has a second electrode electrical capability, the first electrode electrical capability being different than the second electrode electrical capability; the first electrode is formed of a first material and the second electrode is formed of a second material, the first and second materials being non-identical; the first electrode is formed of a conductive material and the second electrode is formed of an insulating material; the device or kit also includes a fourth electrode head removably attachable to the second member, the third electrode head being removably coupled to the second member, the fourth electrode head being configured to apply a current to a tissue, the third and fourth electrode heads being non-identical.

Further aspects, advantages and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 3C is a side schematic view of a portion of still another surgical device having device ends in first positions, in accordance with the principles of the present disclosure;

FIG. 3D is a side schematic view of the portion of the surgical device of FIG. 3C with the device ends in second positions, according to the principles of the present disclosure;

FIG. 3E is a plan view of the portion of the surgical device of FIGS. 3C-3D taken along the lines 3E-3E in FIG. 3D, according to the principles of the present disclosure;

FIG. 4A is a side schematic view of a portion of still another surgical device having a device end in a first position, in accordance with the principles of the present disclosure;

FIG. 6A is a side schematic view of a portion of still another surgical device having device ends in first positions, in accordance with the principles of the present disclosure;

FIG. 6B is a side schematic view of the portion of the surgical device of FIG. 6A with the device ends in second positions, according to the principles of the present disclosure;

FIG. 7A is a perspective view of a portion of still another surgical device having device ends in first positions, in accordance with the principles of the present disclosure;

FIG. 7B is a side schematic view of the portion of the surgical device of FIG. 7A with the device ends in second positions, according to the principles of the present disclosure;

FIG. 9A is a side schematic view of another set of interchangeable device ends for the surgical device kit of FIG. 8, according to the principles of the present disclosure; and FIG. 9B is a side schematic view of yet another set of interchangeable device ends for the surgical device kit of FIG. 8, in accordance with the principles of the present disclosure.

DETAILED DESCRIPTION

Figure 1A:
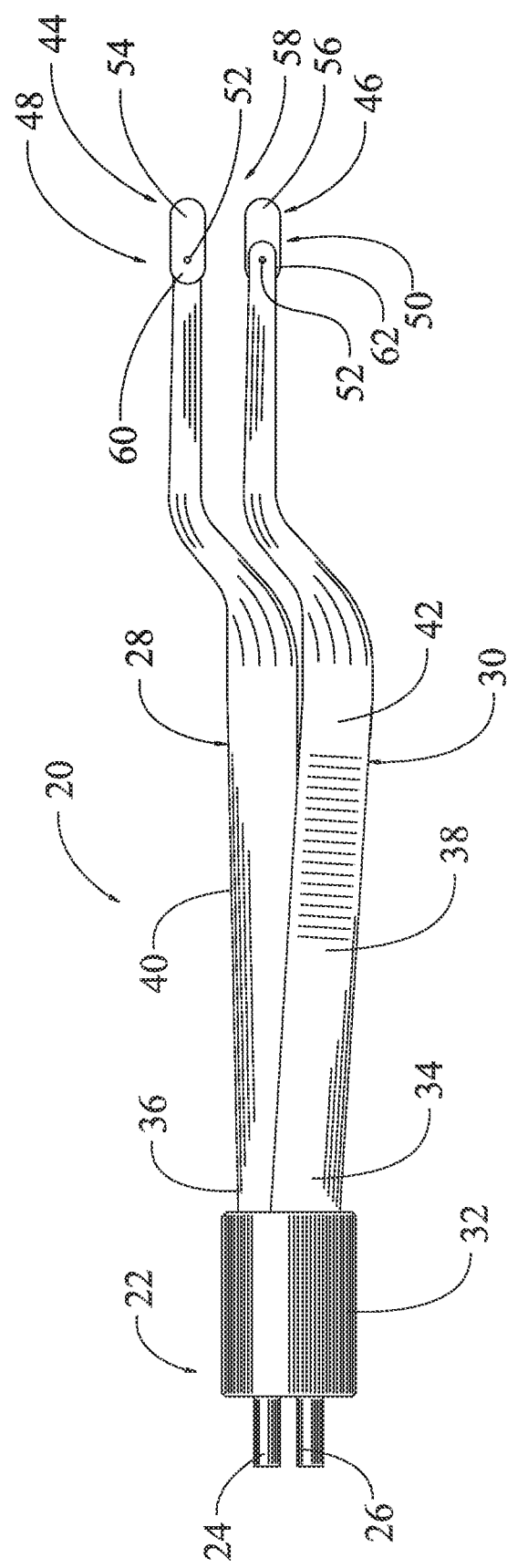
FIG. 1A is a side perspective view of a surgical device having device ends in first positions, in accordance with the principles of the present disclosure.

The following description is merely exemplary in nature and is not intended to limit the present disclosure, application, or uses.

The present disclosure provides a surgical device that has at least one end which may be changeable to fit the needs of various different or same procedures.

For example, referring to FIG. 1, a surgical forceps is illustrated and generally designated at 20. The surgical forceps 20 may be of the electrosurgical type or the non-energized type, by way of example. For example, if of the non-energized type, the forceps 20 are used for gripping and no energy is applied through the forceps 20. However, if the forceps 20 are of the electrosurgical type, they may be used as a bipolar device, for example, to apply pulsed or non-pulsed energy to coagulate a tissue.

For the forceps 20 of the electrosurgical type, the forceps 20 include a proximal end 22 that may be connected to an energy source via first and second leads 24, 26. The forceps 20 may include a first elongate member 28 and a second elongate member 30, which are connected together at the proximal end 22 of the forceps device 20. The first member 28 is disposed adjacent to the second member 30. In this example, a band 32 surrounds proximal ends 34, 36 of the first and second members 28, 30 to couple the proximal ends 34, 36 together. Thus, the proximal ends 34, 36 may be fixed together by the band 32 as shown. In this example, the first and second members 28, 30 are movably coupled together. The first and second members 28, 30 may be moved toward each other by exerting pressure on their outer sides 38, 40; for example, an operator can pinch the first and second members 28, 30 together and toward each other by gripping and exerting pressure on gripping sections 42 disposed on the outer sides 38, 40. (Though not shown, it should be understood that an identical gripping section 42 is disposed on the outer side 40, as shown on the outer side 38.)

The band 32 and the first and second members 28, 30 may be formed of an insulating material, such as a plastic or rubber. In other configurations, the first and second members 28, 30 may each have an inner portion formed of a conductive material, such as a metal, and an outer casing formed of an insulating material, where the outer casing surrounds the inner portion. In still other configurations, such as with non-electrosurgical devices, the first and second members 28, 30 may be formed entirely of a conductive material, such as a metal. This paragraph provides merely examples of materials that may be used for the first and second members 28, 30; other variations not described in this paragraph are also contemplated.

A first end piece 44 is coupled to the distal end 48 of the first member 28, and a second end piece 46 may be coupled to the distal end 50 of the second member 30. In the alternative, the second member 30 may not have a separate end piece 46, but instead, the second member 30 may simply have a non-movable end that may be unitarily formed with the rest of the second member 30. The end pieces 44, 46 may be identical to each other, or the end pieces 44, 46 may be different from each other. The end pieces 44, 46 may take on various configurations, which will be described below.

Figure 1B:
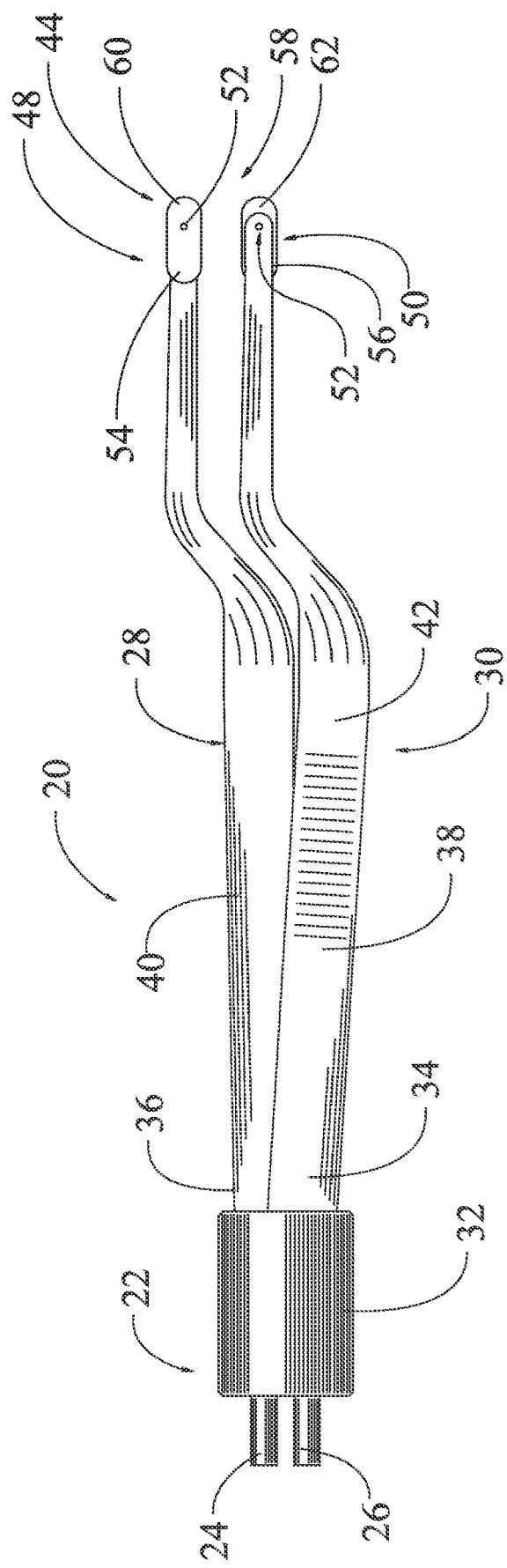
FIG. 1B is a side perspective view of the surgical device of FIG. 1A with the device ends in second positions, according to the principles of the present disclosure.

In the illustrated example of FIGS. 1A-1B, each end piece 44, 46 has a semi-rectangular shape with rounded edges. Each end piece 44, 46 has a joint, such as a pivot pin 52, connecting the end piece 44, 46 to the distal end 48, 50 of the respective member 28, 30.

In FIG. 1A, the first and second end pieces 44, 46 are illustrated in first positions on the first and second members 28, 30, wherein long sides 54, 56 of the end pieces 44, 46 are disposed at the distal end 58 of the device 20. A short side 60 of the first end piece 44 is disposed on an opposite side of the pivot pin 52 from the long side 54. In the first position of the first end piece 44, the short side 60 of the first end piece 44 is disposed closer to the proximal end 22 of the device 20 than the long side 54 is disposed with respect to the proximal end 22. The second end piece 46 may also have a short side 62 that is disposed closer to the proximal end 22 than the long side 56 is disposed with respect to the proximal end 22, in the first position of the second end piece 46.

In FIG. 1B, the first and second end pieces 44, 46 are illustrated in second positions on the first and second members 28, 30, wherein the short sides 60, 62 of the end pieces 44, 46 are disposed at the distal end 58 of the device 20. In the second position of the first member 28, the long side 54 of the first end piece 44 is disposed closer to the proximal end 22 of the device 20 than the short side 60 is disposed with respect to the proximal end 22. The long side 56 of the second end piece 46 is disposed closer to the proximal end 22 than the short side 62 is disposed with respect to the proximal end 22, in the second position of the second member 30. Accordingly, each of the end pieces 44, 46 has a long side 54, 56 and a short side 60, 62, wherein the long and short sides 56, 60 of the first end piece 44 are not identical to each other, and the long and short sides 56, 62 of the second end piece 46 are not identical to each other, since they have different lengths.

The end pieces 44, 46 are movable with respect to the first and second members 28, 30. In the illustrated example, the end pieces 44, 46 are rotatable about the pivot pins 52. In the alternative, another type of joint or connection may be provided. Thus, each end piece 44, 46 may be rotated into their first positions (shown in FIG. 1A) and into their second positions (shown in FIG. 1B). In the example of FIGS. 1A-1B, the first and second end pieces 44, 46 are movable between their first and second positions without being detached from the first and second members 28, 30, respectively, because the end pieces 44, 46 are pivoted around the pivot pins 52, but not detached. Thus, the first end piece 44 is rotatably attached to the first member 28, and the second end piece 46 is rotatably attached to the second member 30. An operator may desire to rotate the end pieces 44, 46 between the first and second positions depending on whether the operator would like to use the long sides 54, 56 or the short sides 60, 62 at the distal end of the device 58. In some examples, each end piece 44, 46 and/or the distal ends 48, 50 of each of the members 28, 30 may have a detent or other feature to aid in positioning the end pieces 44, 46 into the first and second positions.

In some variations, one or more of the end pieces 44, 46 is an electrode. For example, both of the first and second end pieces 44, 46 may be electrodes that are configured to apply a current to a tissue when energized. The first and second end pieces 44, 46 may be active bipolar electrodes that are configured to be coupled with and energized by an electrode energy source. In the illustrated example, the current may be provided through the lead ends 24, 26 and through the pivot pins 52 to each of the end pieces 44, 46.

Figure 2A:
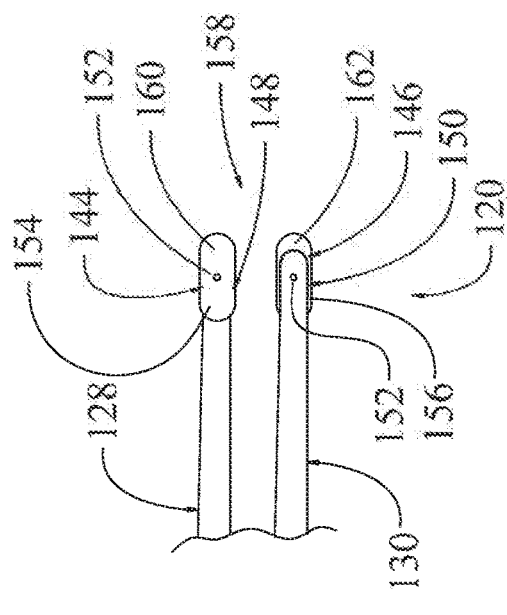
FIG. 2A is a side schematic view of a portion of another surgical device having device ends in first positions, in accordance with the principles of the present disclosure.
Figure 2B:
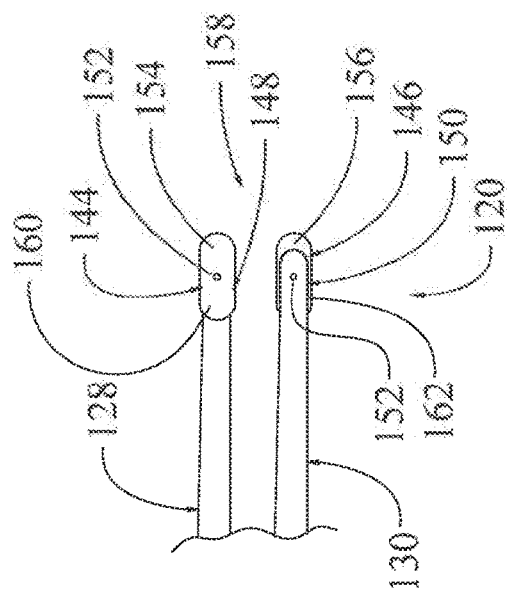
FIG. 2B is a side schematic view of the portion of the surgical device of FIG. 2A with the device ends in second positions, according to the principles of the present disclosure.

Referring now to FIGS. 2A-2B, another example of a portion of a surgical forceps is illustrated and generally designated at 120. The proximal end of the forceps 120 is not shown, however, all details may be the same as shown in FIG. 1A-1B, or the proximal end may take on any other acceptable configuration as known or desired in the art. As in the example of FIGS. 1A-1B, the forceps 120 may be of the electrosurgical type or the non-energized type, by way of example. For example, if of the non-energized type, the forceps 120 are used for gripping and no energy is applied through the forceps 120. However, if the forceps 120 are of the electrosurgical type, they may be used as a bipolar device, for example, to apply pulsed or non-pulsed energy to coagulate a tissue.

The forceps 120 may include a first elongate member 128 and a second elongate member 130, which are connected together at the proximal end (not shown, but may be same or similar as shown in FIGS. 1A-1B). The first member 128 is disposed adjacent to the second member 130. As described above with respect to FIGS. 1A-1B, the first and second members 128, 130 may be moved toward each other by exerting pressure on their outer sides; for example, an operator can pinch the first and second members 128, 130 together and toward each other and bring the end pieces 144, 146 together.

As described above, the first and second members 128, 130 may be formed of an insulating material, such as a plastic or rubber. In other configurations, the first and second members 128, 130 may each have an inner portion formed of a conductive material, such as a metal, and an outer casing formed of an insulating material, where the outer casing surrounds the inner portion. In still other configurations, such as non electrosurgical devices, the first and second members 128, 130 may be formed entirely of a conductive material, such as a metal.

The first end piece 144 is coupled to the distal end 148 of the first member 128, and the second end piece 146 may be coupled to the distal end 150 of the second member 130. In the alternative, the second member may not have a separate end piece 146. The end pieces 144, 146 may be identical to each other, or the end pieces 144, 146 may be different from each other.

In the illustrated example of FIGS. 2A-2B, each end piece 144, 146 has a semi-rectangular shape with rounded edges. Each end piece 144, 146 has a joint, such as a pivot pin 152, connecting the end piece 144, 146 to the distal end 148, 150 of the respective member 128, 130.

In FIG. 2A, the first and second end pieces 144, 146 are illustrated in first positions on the first and second members 128, 130, wherein a first side 154, 156 of each of the end pieces 144, 146 is disposed at the distal end 158 of the device 120. A second side 160 of the first end piece 144 is disposed on an opposite side of the pivot pin 152 from the first side 154. In the first position of the first end piece 144, the second side 160 of the first end piece 144 is disposed closer to the proximal end (not shown) of the device 120 than the first side 154 is disposed with respect to the proximal end. The second end piece 146 may also have a second side 162 that is disposed closer to the proximal end than the first side 156 is disposed with respect to the proximal end, in the first position of the second end piece 146.

In FIG. 2, the first and second end pieces 144, 146 are illustrated in second positions on the first and second members 128, 130, wherein the second sides 160, 162 of the end pieces 144, 146 are disposed at the distal end 158 of the device 120. In the second position of the first end piece 144, the first side 154 of the first end piece 144 is disposed closer to the proximal end (not shown) of the device 120 than the second side 160 is disposed with respect to the proximal end. The first side 156 of the second end piece 146 is disposed closer to the proximal end than the second side 162 is disposed with respect to the proximal end, in the second position of the second end piece 146.

The first and second sides 154, 160 of the first end piece 144 are identical to each other, each being disposed on opposite sides of the pivot pin 152. Likewise, the first and second sides 156, 162 of the second end piece 146 are identical to each other, each being disposed on opposite sides of the pivot pin 152.

The end pieces 144, 146 are movable with respect to the first and second members 128, 130. In the illustrated example, the end pieces 144, 146 are rotatable about the pivot pins 152. Thus, each end piece 144, 146 may be rotated into their first positions (shown in FIG. 2A) and into their second positions (shown in FIG. 2B). In the example of FIGS. 2A-2B, the first and second end pieces 144, 146 are movable between their first and second positions without being detached from the first and second members 128, 130, respectively, because the end pieces 144, 146 are pivoted around the pivot pins 152. Thus, the first end piece 144 is rotatably attached to the first member 128, and the second end piece 146 is rotatably attached to the second member 130. An operator may desire to rotate the end pieces 144, 146 between the first and second positions if one of the sides 154, 156, 160, 162 has become dirty or damaged. Thus, the operator could continue to use the forceps device 120 even if one side 154, 156, 160, 162 of an end piece 164, 166 becomes undesirable for use.

As in the example of FIGS. 1A-1B, one or more of the end pieces 144, 146 could be provided as an electrode. For example, both of the first and second end pieces 144, 146 may serve as electrodes that are configured to apply a current to a tissue when energized. The first and second end pieces 144, 146 may be active bipolar electrodes that are configured to be coupled with and energized by an electrode energy source. In the illustrated example, the current may be provided through lead ends (such as lead ends 24, 26 shown in FIGS. 1A-1B) and through the pivot pins 152 to each of the end pieces 144, 146.

Figure 3A:
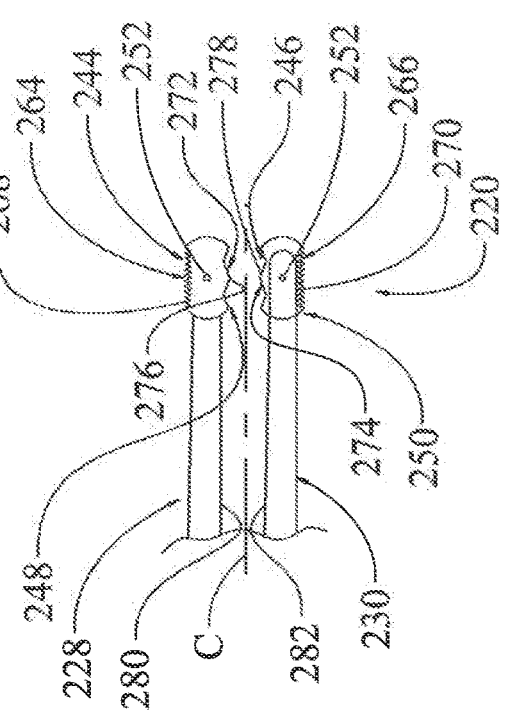
FIG. 3A is a side schematic view of a portion of yet another surgical device having device ends in first positions, in accordance with the principles of the present disclosure.
Figure 3B:
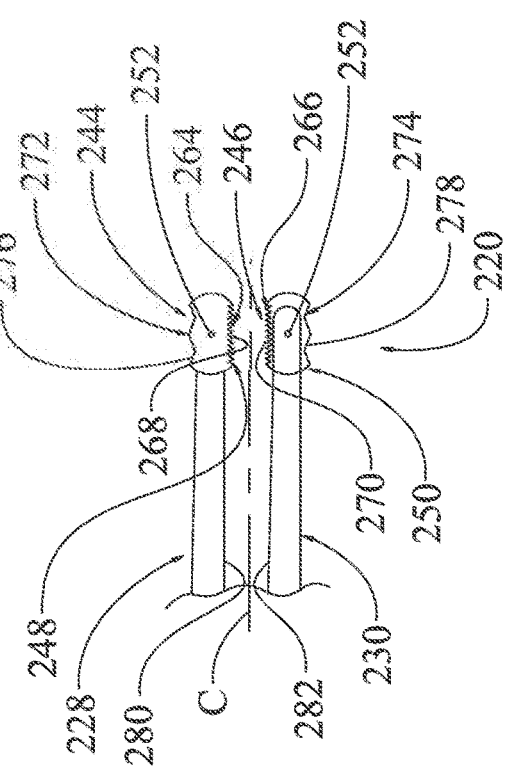
FIG. 3B is a side schematic view of the portion of the surgical device of FIG. 3A with the device ends in second positions, according to the principles of the present disclosure.

Referring now to FIGS. 3A-3B, another example of a portion of a surgical forceps is illustrated and generally designated at 220. The proximal end of the forceps 220 is not shown, however, all details may be the same as shown in FIG. 1A-1B, or the proximal end may take on any other acceptable configuration as known in the art. As in the examples of FIGS. 1A-1B and 2A-2B, the forceps 220 may be of the electrosurgical type or the non-energized type, by way of example. For example, if of the non-energized type, the forceps 220 are used for gripping and no energy is applied through the forceps 220. However, if the forceps 220 are of the electrosurgical type, they may be used as a bipolar device, for example, to apply pulsed or non-pulsed energy to coagulate a tissue.

The forceps 220 may include a first elongate member 228 and a second elongate member 230, which are connected together at a proximal end (not shown). The first member 228 is disposed adjacent to the second member 230. As described above with respect to FIGS. 1A-1B, the first and second members 228, 230 may be moved toward each other by exerting pressure on their outer sides; for example, an operator can pinch the first and second members 228, 230 together and toward each other and bring the end pieces 244, 246 together.

As described above, the first and second members 228, 230 may be formed of an insulating material, such as a plastic or rubber. In other configurations, the first and second members 228, 230 may each have an inner portion formed of a conductive material, such as a metal, and an outer casing formed of an insulating material, where the outer casing surrounds the inner portion. In still other configurations, such as non electrosurgical devices, the first and second members 228, 230 may be formed entirely of a conductive material, such as a metal, by way of example.

The first end piece 244 is coupled to the distal end 248 of the first member 228, and the second end piece 246 may be coupled to the distal end 250 of the second member 230. In the alternative, the second member 230 may not have a separate end piece 246, as described above. The end pieces 244, 246 may be identical to each other, or the end pieces 244, 246 may be different from each other.

In the illustrated example of FIGS. 3A-3B, each end piece 244, 246 has a first set of teeth 264, 266 disposed on a first side 268, 270 and a second set of teeth 272, 274 disposed on a second side 276, 278. The first sides 268, 270 are disposed on opposite elongate faces of the end pieces 244, 246 from the second sides 276, 278. Each end piece 244, 246 has a joint, such as a pivot pin 252, connecting the end piece 244, 246 to the distal end 248, 250 of the respective member 228, 230.

In FIG. 3A, the first and second end pieces 244, 246 are illustrated in first positions on the first and second members 228, 230, wherein the first sets of teeth 264, 266 of each of the end pieces 244, 246 are disposed facing each other and facing toward a central axis C of the device 220, the central axis C being disposed between inner sides 280, 282 of each of the first and second members 228, 230. In the first positions, the second sets of teeth 272, 274 are facing outwardly and away from the central axis C. In other examples, one of the members 228, 230 or end pieces 244, 246 may be plain without a set of teeth, so that the teeth only appear on the end 248, 250 of one of the members 228, 230.

In FIG. 3B, the first and second end pieces 244, 246 are illustrated in second positions on the first and second members 228, 230, wherein the second sets of teeth 272, 274 of each of the end pieces 244, 246 are disposed facing each other and facing toward a central axis C of the device 220. In the second positions, the first sets of teeth 264, 266 are facing outwardly and away from the central axis C.

In some variations, the first and second sets of teeth 264, 272, of the first end piece 244 may be identical to each other, each being disposed on opposite sides of the pivot pin 252. Likewise, the first and second sets of teeth 266, 274 of the second end piece 246 may be identical to each other, each being disposed on opposite sides of the pivot pin 252. However, as illustrated in FIGS. 3A-3B, the first sets of teeth 264, 266 in this example have a larger number and smaller teeth than the second sets of teeth 272, 274. The second sets of teeth 272, 274 have a smaller number and are larger than the first sets of teeth 264, 266.

The end pieces 244, 246 are movable with respect to the first and second members 228, 230. In the illustrated example, the end pieces 244, 246 are rotatable about the pivot pins 252. Thus, each end piece 244, 246 may be rotated into their first positions (shown in FIG. 3A) and into their second positions (shown in FIG. 3B). In the example of FIGS. 3A-3B, the first and second end pieces 244, 246 are movable between their first and second positions without being detached from the first and second members 228, 230, respectively, because the end pieces 244, 246 are pivoted around the pivot pins 252. Thus, the first end piece 244 is rotatably attached to the first member 228, and the second end piece 246 is rotatably attached to the second member 230.

An operator may desire to rotate the end pieces 244, 246 between the first and second positions if one of the sets of teeth 264, 266, 272, 274 has become dirty or damaged. Furthermore, the operator may desire to rotate the end pieces 244, 246 to use either the smaller or larger sets of teeth 264, 266, 272, 274, depending on the application, without having to use a different set of forceps.

As in the examples of FIGS. 1A-2B, one or more of the end pieces 244, 246 could be provided as an electrode. For example, both of the first and second end pieces 244, 246 may serve as electrodes that are configured to apply a current to a tissue when energized. The first and second end pieces 244, 246 may be active bipolar electrodes that are configured to be coupled with and energized by an electrode energy source. In the illustrated example, the current may be provided through lead ends (such as lead ends 24, 26 shown in FIGS. 1A-1B) and through the pivot pins 252 to each of the end pieces 244, 246.

Referring now to FIGS. 3C-3E, another example of a portion of a surgical forceps is illustrated and generally designated at 1220. The proximal end of the forceps 1220 is not shown, however, all details may be the same as shown in FIG. 1A-1B, or the proximal end may take on any other acceptable configuration as known in the art. The forceps 1220 may be essentially the same as the forceps 220 described above with respect to FIGS. 3A-3B, except for the orientation of the teeth 1264, 1266, 1272, 1274, which will be described below. For example, the forceps 1220 may include a first elongate member 1228, a second elongate member 1230, and pins 1252 holding the rotatable device ends 1244, 1246 to the distal ends 1248, 1250 of the first and second members 1228, 1230. In addition, the device ends 1244, 1246 may or may not be provided as energizable electrodes.

In the illustrated example of FIGS. 3C-3E, each end piece 1244, 1246 has a first set of teeth 1264, 1266 disposed on a first end 1269, 1271 and a second set of teeth 1272, 1274 disposed on a second end 1277, 1279 of the device ends 1244, 1246. Each of the sets of teeth 1264, 1266, 1272, 1274 is disposed on a first face 1268, 1270 of each device end 1244, 1246. Second faces 1276, 1278 of the end pieces 1244, 1246 are disposed on opposite sides of the end pieces 1244, 1246 from the first faces 1268, 1270. The second faces 1276, 1278 are flat and have no teeth, in this example.

In FIG. 3C, the first and second end pieces 1244, 1246 are illustrated in first positions on the first and second members 1228, 1230, wherein the first sets of teeth 1264, 1266 are disposed facing each other and facing toward a central axis C of the device 1220, the central axis C being disposed between inner sides 1280, 1282 of each of the first and second members 1228, 1230. In the first positions, the first sets of teeth 1264, 1266 and the first ends 1269, 1271 of the device ends 1244, 1246 are disposed at the distal end 1258 of the forceps 1220. The second sets of teeth 1272, 1274 are not facing directly toward to the central axis C, as the second sets of teeth 1272, 1274 are oriented on angle in the first positions. More particularly, the distal ends 1248, 1250 of the first and second members 1228, 1230 are angled inward toward the central axis C. As such, in the first positions, the first sets of teeth 1264, 1266 are aligned along parallel planes and are configured to compress tissue therebetween when the first and second members 1228, 1230 are pressed toward each other and toward the central axis C. The second sets of teeth 1272, 1274 are disposed along non-parallel planes in the first positions, and the second sets of teeth 1272, 1274 are configured to be spaced farther from each other than the first sets of teeth 1264, 1266 are spaced with respect to each other. As such, the second sets of teeth 1272, 1274 are configured to remain apart from each and not grasp tissue in the first positions, even when the first and second members 1228, 1230 are pressed toward each other.

In FIGS. 3D-3E, the first and second end pieces 1244, 1246 are illustrated in second positions on the first and second members 1228, 1230. The second sets of teeth 1272, 1274 and the second ends 1277, 1279 of the device ends 1244, 1246 are disposed at the distal end 1258 of the forceps 1220. In the second positions, the second sets of teeth 1272, 1274 are directly facing each other and facing toward the central axis C of the device 1220. In the second positions, the second sets of teeth 1272, 1274 are aligned along parallel planes and are configured to compress tissue therebetween when the first and second members 1228, 1230 are pressed toward each other. The first sets of teeth 1264, 1266 are disposed along non-parallel planes in the second positions, and the first sets of teeth 1264, 1266 are configured to be spaced farther from each other than the second sets of teeth 1272, 1274 are spaced with respect to each other. As such, the first sets of teeth 1264, 1266 are configured to remain apart from each and not grasp tissue in the second positions, even when the first and second members 1228, 1230 are pressed toward each other.

In some variations, the first and second sets of teeth 1264, 1272, of the first end piece 1244 may be identical to each other, each being disposed on opposite sides of the pivot pin 1252. Likewise, the first and second sets of teeth 1266, 1274 of the second end piece 1246 may be identical to each other, each being disposed on opposite sides of the pivot pin 1252. However, as illustrated in FIGS. 3C-3E, the first sets of teeth 1264, 1266 in this example have a larger number and smaller teeth than the second sets of teeth 1272, 1274. The second sets of teeth 1272, 1274 have a smaller number and are larger than the first sets of teeth 1264, 1266.

The end pieces 1244, 1246 are movable with respect to the first and second members 1228, 1230. In the illustrated example, the end pieces 1244, 1246 are rotatable about the pivot pins 1252. Thus, each end piece 1244, 1246 may be rotated into their first positions (shown in FIG. 3C) and into their second positions (shown in FIGS. 3D-3E). In FIGS. 3A-3B, the end pieces 244, 246 are pivotable along a first plane that is perpendicular to the central axis C, while in FIGS. 3C-3E, the end pieces 1244, 1246 are pivotable along a second plane that is not perpendicular to the central axis C. Because the distal ends 1248, 1250 of the first and second members 1228, 1230 are angled with respect to the central axis C, the second plane is not parallel to the central axis C, but the second plane is disposed at an acute angle with respect to the central axis C.

An operator may desire to rotate the end pieces 1244, 1246 between the first and second positions if one of the sets of teeth 1264, 1266, 1272, 1274 has become dirty or damaged. Furthermore, the operator may desire to rotate the end pieces 1244, 1246 to use either the smaller or larger sets of teeth 1264, 1266, 1272, 1274, depending on the application, without having to use a different set of forceps.

Figure 4C:
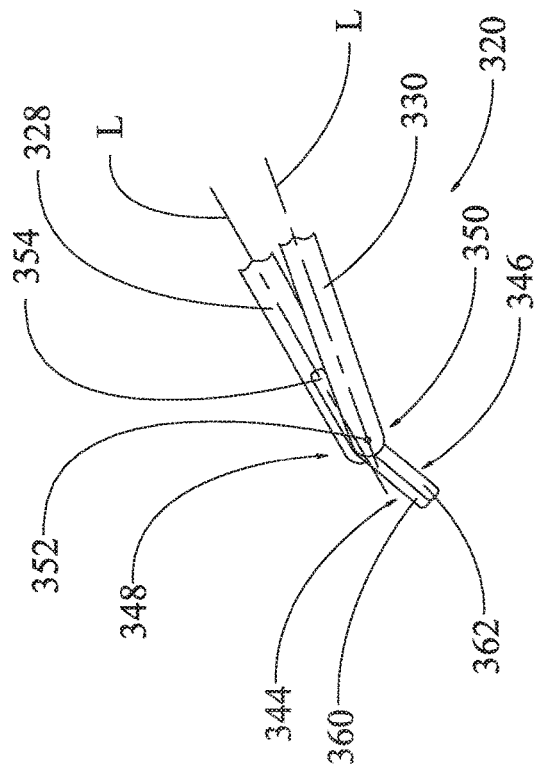
FIG. 4C is a perspective view of a portion of the surgical device of FIGS. 4A-4B, with two device ends in the second position, according to the principles of the present disclosure.
Figure 4B:
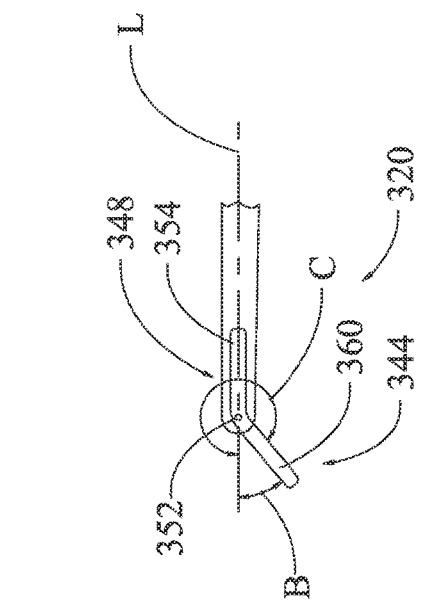
FIG. 4B is a side schematic view of the portion of the surgical device of FIG. 4A with the device end in a second position, according to the principles of the present disclosure.

Referring now to FIGS. 4A-4C, another example of a portion of a surgical forceps is illustrated and generally designated at 320. The proximal end of the forceps 320 is not shown, however, all details may be the same as shown in FIG. 1A-1B, or the proximal end may take on any other acceptable configuration as known in the art. As in the examples of FIGS. 1A-3B, the forceps 320 may be of the electrosurgical type or the non-energized type, by way of example. For example, if of the non-energized type, the forceps 320 are used for gripping and no energy is applied through the forceps 320. However, if the forceps 320 are of the electrosurgical type, they may be used as a bipolar device, for example, to apply pulsed or non-pulsed energy to coagulate a tissue.

The forceps 320 may include a first elongate member 328 and a second elongate member 330 (shown in FIG. 4C). The second elongate member 330 may be understood to be either identical to the first elongate member 328, or the second elongate member 330 may be plain without a pivotable end piece 346; however, preferably, the second elongate member 330 has a pivotable end piece 346. The first member 328 and the second member 330 may be connected together at the proximal end (not shown). The first member 328 is disposed adjacent to the second member 330. As described above with respect to FIGS. 1A-1B, the first member 328 and the second member 330 may be moved toward each other by exerting pressure on their outer sides; for example, an operator can pinch the first member 328 and the second member 330 together and toward each other and bring the first end piece 344 and the end of the second member 330 together (whether the second member 330 has an end piece 346 or no end piece).

As described above, the first member 328 and the second member 330 may be formed of an insulating material, such as a plastic or rubber. In other configurations, the first member 328 and the second member 330 may each have an inner portion formed of a conductive material, such as a metal, and an outer casing formed of an insulating material, where the outer casing surrounds the inner portion. In still other configurations, such as non-electrosurgical devices, the first member 328 and the second member 330 may be formed entirely of a conductive material, such as a metal.

The first end piece 344 is coupled to the distal end 348 of the first member 328. The second member 330 may also have an end piece 346 identical or different from the first end piece 344, which may be coupled to the distal end 350 of the second member 330.

Each end piece 344, 346 has a joint, such as a pivot pin 352, connecting the end piece 344, 346 to the distal end 348, 350 of the respective member 328, 330. The end pieces 344, 346 may be rotated around the pivot pins 352 to move the end pieces 344, 346 into various positions, such as first and second positions. FIGS. 4A-4B illustrate first and second positions of the first end piece 344, and it should be understood that the second end piece 346 may also be rotated into first and second positions, as is shown with respect to the first end piece 344.

In FIG. 4A, the first end piece 344 is illustrated in a first position on the first member 328, wherein the first end piece has a first part 354 that extends at an angle A with respect to a longitudinal axis L defined by the distal end 348 of the first member 328. In the first position, a second part 360 of the first end piece 344 is disposed along the longitudinal axis L, in this example.

In FIG. 3B, the first end piece 344 is illustrated in a second position on the first member 328, wherein the second part 360 of the first end piece 344 extends at an angle B with respect to the longitudinal axis L. In the second position, the first part 354 of the first end piece 344 is disposed along the longitudinal axis L.

The angle B may be equal or different from the angle A, in either or both of magnitude and direction. For example, the angle A may be defined as extending in a positive direction from the axis L. Accordingly, it can be seen that the angle A is a positive acute angle in FIG. 4A. As such, the angle B is shown as extending in the opposite direction from the longitudinal axis L, in a negative direction, as shown in FIG. 4B. Thus, if the angles were instead both measured in a positive direction, then the second part 360 would extend at an angle C from the longitudinal axis L, and the angle C would clearly be an obtuse angle much larger than the angle A.

FIG. 4C shows both first and second pieces 344, 346 in the second positions. Thus, the second part 360 of the first end piece 344 extends at the angle B or C from the longitudinal axis L in the second position as shown in FIG. 4C, and the second part 362 of the second end piece 346 extends at an angle, such as B or C, from a longitudinal axis $L_2$ defined by the distal end 350 of the second member 330 in the second position as shown in FIG. 4C. It should be noted that in the second positions of both the first and second end pieces 344, 346, both the second parts 360, 362 extend at the same angle, such as B, from their respective longitudinal axes L, $L_2$, in the illustrated example. As such, the second parts 360, 362 are disposed alongside each other and can be used to grip a piece of tissue.

The end pieces 344, 346 are movable with respect to the first and second members 328, 330. In the illustrated example, the end pieces 344, 346 are rotatable about the pivot pins 352. Thus, each end piece 344, 346 may be rotated into their first positions (the first position of the first end piece 344 is shown in FIG. 4A; the second end piece may have an identical first position) and into their second positions (shown in FIGS. 4B-4C). In the example of FIGS. 4A-4C, the first and second end pieces 344, 346 are movable between their first and second positions without being detached from the first and second members 328, 330, respectively, because the end pieces 344, 346 are pivoted around the pivot pins 352. Thus, the first end piece 344 is rotatably attached to the first member 328, and the second end piece 346 is rotatably attached to the second member 330.

An operator may desire to rotate the end pieces 344, 346 between the first and second positions if one of the parts 354, 360, 356, 362 has become dirty or damaged. Furthermore, the operator may desire to rotate the end pieces 344, 346 so that the end pieces 344, 346 have parts extending at a desired angle or in a desired direction from the axis L, depending on the application, without having to use a different set of forceps.

As in the examples of FIGS. 1A-3B, one or more of the end pieces 344, 346 could be provided as an electrode. For example, both of the first and second end pieces 344, 346 may serve as electrodes that are configured to apply a current to a tissue when energized. The first and second end pieces 344, 346 may be active bipolar electrodes that are configured to be coupled with and energized by an electrode energy source. In the illustrated example, the current may be provided through lead ends (such as lead ends 24, 26 shown in FIGS. 1A-1B) and through the pivot pins 352 to each of the end pieces 344, 346.

Figure 5B:
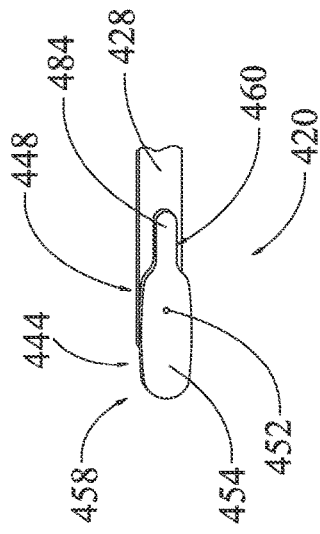
FIG. 5B is a side schematic view of the portion of the surgical device of FIG. 5A with the device end in a second position, according to the principles of the present disclosure.
Figure 5A:
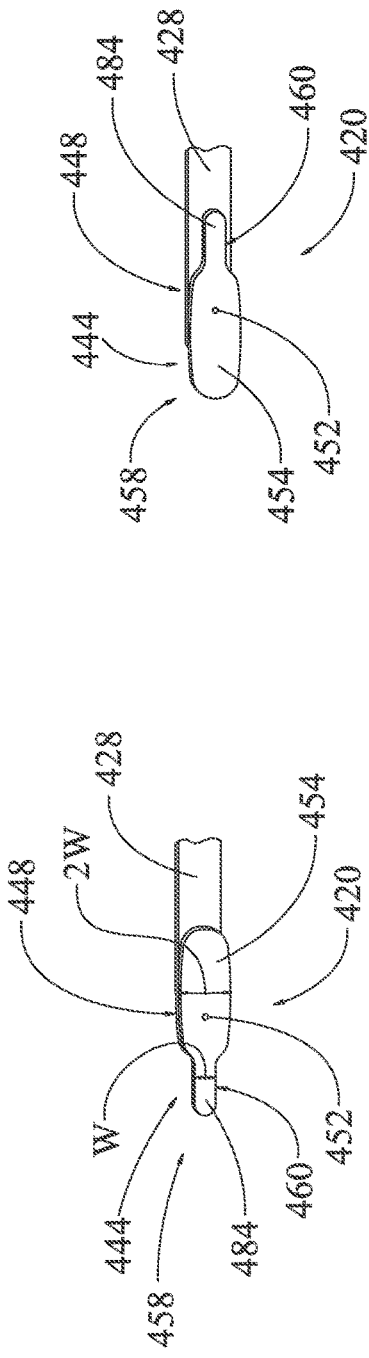
FIG. 5A is a side schematic view of a portion of still another surgical device having a device end in a first position, in accordance with the principles of the present disclosure.

Referring now to FIGS. 5A-5B, another example of a portion of a surgical forceps is illustrated and generally designated at 420. The proximal end of the forceps 420 is not shown, however, all details may be the same as shown in FIG. 1A-1B, or the proximal end may take on any other acceptable configuration as known in the art. As in the example of FIGS. 1A-1B, the forceps 420 may be of the electrosurgical type or the non-energized type, by way of example. For example, if of the non-energized type, the forceps 420 are used for gripping and no energy is applied through the forceps 420. However, if the forceps 420 are of the electrosurgical type, they may be used as a bipolar device, for example, to apply pulsed or non-pulsed energy to coagulate a tissue.

The forceps 420 may include a first elongate member 428 and a second elongate member (not shown), which are connected together at the proximal end (not shown). Though the second member is not shown, it may be the same as or similar to the first member 428 and connected as shown in FIGS. 1A-1B, by way of example. The first member 428 is disposed adjacent to the second member. As described above with respect to FIGS. 1A-1B, the first member 428 and the second member may be moved toward each other by exerting pressure on their outer sides; for example, an operator can pinch the first member 428 and the second member together and toward each other and bring the first end piece 444 and the end of the second member together. The second member may have an identical end piece 444, another end piece, or no end piece.

As described above, the first member 428 and the second member may be formed of an insulating material, such as a plastic or rubber. In other configurations, the first member 428 and the second member may each have an inner portion formed of a conductive material, such as a metal, and an outer casing formed of an insulating material, where the outer casing surrounds the inner portion. In still other configurations, such as non-electrosurgical devices, the first member 428 and the second member may be formed entirely of a conductive material, such as a metal, by way of example.

The first end piece 444 is coupled to the distal end 448 of the first member 428. A similar end may be coupled to the second member. In the alternative, the second member may not have a separate end piece. The first end piece 444 and the second end piece may be identical to each other, or the first end piece 444 and the second end piece may be different from each other.

In the illustrated example of FIGS. 5A-5B, the end piece 444 has a first wide part 454 and a second part 460 that has a narrow projection 484. In this example, the narrow projection 484 has a width w that is half the width of the first part 454. Thus, the width of the first part 454 is 2 w. In other examples, the narrow projection width w could be smaller than the width of the first part, but not as small as half the width of the first part. In still other examples, the width of the narrow projection 484 could be less than half as wide as the width of the first part 454. The end piece 444 has a joint, such as a pivot pin 452, connecting the end piece 444 to the distal end 448 of the first member 428.

In FIG. 5A, the end piece 444 is illustrated in a first position on the first members 428, wherein the projection 484 of the end piece 444 is disposed at the distal end 458 of the device 420. The first side 454 of the end piece 444 is disposed on an opposite side of the pivot pin 452 from the second side 460 and the projection 484. In the first position of the end piece 444, the first side 454 of the end piece 444 is disposed closer to the proximal end (not shown) of the device 420 than the second side 460 is disposed with respect to the proximal end. The second member and end piece (not shown), may also have a similar first position.

In FIG. 5B, the end piece 444 is illustrated in a second position on the first member 428, wherein the first side 454 of the end piece 444 is disposed at the distal end 458 of the device 420. In the second position of the end piece 444, the second side 460 of the end piece 444 is disposed closer to the proximal end (not shown) of the device 420 than the first side 454 is disposed with respect to the proximal end. The second member and end piece (not shown), may also have a similar second position.

The end piece 444 is movable with respect to the first member 428. In the illustrated example, the end piece 444 is rotatable about the pivot pin 452. Thus, the end piece 444 may be rotated into the first position (shown in FIG. 5A) and into the second position (shown in FIG. 5B). In the example of FIGS. 5A-5B, the end piece 444 is movable between the first and second positions without being detached from the first member 428, because the end piece 444 is pivoted around the pivot pin 452. Thus, the end piece 444 is rotatably attached to the first member 428. Likewise, an identical second end piece (not shown) may be rotatably attached to the second member (not shown).

An operator may desire to rotate the end pieces 444 between the first and second positions if one of the sides 454, 460 has become dirty or damaged. Thus, the operator could continue to use the forceps device 420 even if one side 454, 460 has become undesirable for use. Furthermore, the first and second sides 454, 460 of the end piece 444 are of different sizes, they have different widths (as described above), and they have different surface areas. The operator may desire to use the wider side 454 or the narrower side 460 for different applications, without having to use a different forceps.

As in the example of FIGS. 1A-1B, the end piece 444 could be provided as an electrode. For example, both of the first and second end pieces 444 (second end piece not shown), may serve as electrodes that are configured to apply a current to a tissue when energized. The first and second end pieces 444 (second end piece not shown) may be active bipolar electrodes that are configured to be coupled with and energized by an electrode energy source. In the illustrated example, the current may be provided through lead ends (such as lead ends 24, 26 shown in FIGS. 1A-1B) and through pivot pins 452 to each of the end pieces 444 (second end piece not shown).

Referring now to FIGS. 6A-6B, another example of a portion of a surgical forceps is illustrated and generally designated at 520. The proximal end of the forceps 520 is not shown, however, all details may be the same as shown in FIG. 1A-1B, or the proximal end may take on any other acceptable configuration as known in the art. As in the examples of FIGS. 1A-5B, the forceps 520 may be of the electrosurgical type or the non-energized type, by way of example. For example, if of the non-energized type, the forceps 520 are used for gripping and no energy is applied through the forceps 520. However, if the forceps 520 are of the electrosurgical type, they may be used as a bipolar device, for example, to apply pulsed or non-pulsed energy to coagulate a tissue.

The forceps 520 may include a first elongate member 528 and a second elongate member 530, which are connected together at the proximal end (not shown). The first member 528 is disposed adjacent to the second member 530. As described above with respect to FIGS. 1A-1B, the first and second members 528, 530 may be moved toward each other by exerting pressure on their outer sides; for example, an operator can pinch the first and second members 528, 530 together and toward each other and bring the end pieces 544, 546 together.

As described above, the first and second members 528, 530 may be formed of an insulating material, such as a plastic or rubber. In other configurations, the first and second members 528, 530 may each have an inner portion formed of a conductive material, such as a metal, and an outer casing formed of an insulating material, where the outer casing surrounds the inner portion. In still other configurations, such as non-electrosurgical devices, the first and second members 528, 530 may be formed entirely of a conductive material, such as a metal, by way of example.

The first end piece 544 is coupled to the distal end 548 of the first member 528, and the second end piece 546 may be coupled to the distal end 550 of the second member 530. In the alternative, the second member 530 may not have a separate end piece 546. The end pieces 544, 546 may be identical to each other, as shown, or the end pieces 544, 546 may be different from each other.

In the illustrated example of FIGS. 6A-6B, each end piece 544, 546 has a sharp edge 586, 588 disposed on a first part 554, 556 and a dull edge 590, 592 disposed on a second part 560, 562. Each end piece 544, 546 has a joint, such as a pivot pin 552, connecting the end piece 544, 546 to the distal end 548, 550 of the respective member 528, 530.

In FIG. 6A, the first and second end pieces 544, 546 are illustrated in first positions on the first and second members 528, 530, wherein the first parts 454, 456 of the end pieces 544, 546 having the sharp edges 586, 588 are disposed at the distal end 558 of the device 520. The second part 560 of the first end piece 544 is disposed on an opposite side of the pivot pin 552 from the first part 554. In the first position of the first end piece 544, the second part 560 of the first end piece 544 is disposed closer to the proximal end (not shown) of the device 520 than the first part 554 is disposed with respect to the proximal end. Likewise, the second part 562 of the second end piece 546 is disposed on an opposite side of the pivot pin 552 from the first part 556. In the first position of the second end piece 544, the second part 562 of the second end piece 546 is disposed closer to the proximal end (not shown) of the device 520 than the first part 556 is disposed with respect to the proximal end.

In FIG. 6B, the first and second end pieces 544, 546 are illustrated in second positions on the first and second members 528, 530, wherein the second parts 560, 562 of the end pieces 544, 546 having the dull sides 590, 592 are disposed at the distal end 558 of the device 520. In the second position of the first member 528, the first part 554 of the first end piece 544 is disposed closer to the proximal end (not shown) of the device 520 than the second part 560 is disposed with respect to the proximal end. The first part 556 of the second end piece 546 is disposed closer to the proximal end than the second part 562 is disposed with respect to the proximal end, in the second position of the second member 530.

Accordingly, each of the end pieces 544, 546 have a sharp edge 586, 588 and a dull edge 590, 592, wherein the sharp and dull edges 586, 590 of the first end piece 544 are not identical to each other, the sharp edge 586 being sharper than the dull edge 590. Likewise, the sharp and dull edges 588, 592 of the second end piece 546 are not identical to each other, the sharp edge 588 being sharper than the dull edge 592.

The end pieces 544, 546 are movable with respect to the first and second members 528, 530. In the illustrated example, the end pieces 544, 546 are rotatable about the pivot pins 552. Thus, each end piece 544, 546 may be rotated into their first positions (shown in FIG. 6A) and into their second positions (shown in FIG. 68). In the example of FIGS. 6A-6B, the first and second end pieces 544, 546 are movable between their first and second positions without being detached from the first and second members 528, 530, respectively, because the end pieces 544, 546 are pivoted around the pivot pins 552. Thus, the first end piece 544 is rotatably attached to the first member 528, and the second end piece 546 is rotatably attached to the second member 530.

An operator may desire to rotate the end pieces 544, 546 between the first and second positions if one of the parts 554, 556, 560, 562 has become dirty or damaged. Furthermore, the operator may desire to rotate the end pieces 544, 546 to use either the sharp edges 586, 588 or the parts 560, 562 having dull edges 590, 592 on a particular application, without having to use a different set of forceps for different tasks.

As in the examples of FIGS. 1A-5B, one or more of the end pieces 544, 546 could be provided as an electrode. For example, both of the first and second end pieces 544, 546 may serve as electrodes that are configured to apply a current to a tissue when energized. The first and second end pieces 544, 546 may be active bipolar electrodes that are configured to be coupled with and energized by an electrode energy source. In the illustrated example, the current may be provided through lead ends (such as lead ends 24, 26 shown in FIGS. 1A-1B) and through the pivot pins 552 to each of the end pieces 544, 546.

Referring now to FIGS. 7A-7B, another example of a portion of a surgical forceps is illustrated and generally designated at 620. The proximal end of the forceps 620 is not shown, however, all details may be the same as shown in FIG. 1A-1B, or the proximal end may take on any other acceptable configuration as known in the art. As in the examples of FIGS. 1A-6B, the forceps 620 may be of the electrosurgical type or the non-energized type, by way of example. For example, if of the non-energized type, the forceps 620 are used for gripping and no energy is applied through the forceps 620. However, if the forceps 620 are of the electrosurgical type, they may be used as a bipolar device, for example, to apply pulsed or non-pulsed energy to coagulate a tissue.

The forceps 620 may include a first elongate member 628 and a second elongate member 630, which are connected together at the proximal end (not shown). The first member 628 is disposed adjacent to the second member 630. As described above with respect to FIGS. 1A-1B, the first and second members 628, 630 may be moved toward each other by exerting pressure on their outer sides; for example, an operator can pinch the first and second members 628, 630 together and toward each other and bring the end pieces 644, 646 together.

As described above, the first and second members 628, 630 may be formed of an insulating material, such as a plastic or rubber. In other configurations, the first and second members 628, 630 may each have an inner portion formed of a conductive material, such as a metal, and an outer casing formed of an insulating material, where the outer casing surrounds the inner portion. In still other configurations, such as non-electrosurgical devices, the first and second members 628, 630 may be formed entirely of a conductive material, such as a metal, by way of example.

The first end piece 644 is coupled to the distal end 648 of the first member 628, and the second end piece 646 may be coupled to the distal end 650 of the second member 630. In the alternative, the second member 630 may not have a separate end piece 646, as described above. The end pieces 644, 646 may be identical to each other, as shown, or the end pieces 644, 646 may be different from each other.

Each end piece 644, 646 has a first part 654, 656 that is fixedly attached to the distal ends 648, 650 of the first and second members 628, 630, respectively. In some examples, the first parts 654, 656 may be formed unitarily with the distal ends 648, 650, respectively. A second part 660 of the first end piece 644 is movable with respect to the first part 654 and the first member 628. Likewise, a second part 662 of the second end piece 646 is movable with respect to the first part 656 and the second member 630. For example, the first parts 654, 656 may each define a bore 694, 696 therein, the first parts 654, 656 defining an opening 698, 699 in distal ends 700, 701 of the first parts 654, 656, the openings 698, 699 forming a distal end of the bores 694, 696. The second parts 660, 662 may be retractable or slidable into and out of the openings 698, 699 of the bores 694, 696. Thus, the second parts 660, 662 are axially movable with respect to the first parts 654, 656.

In FIG. 7A, the first and second end pieces 644, 646 are illustrated in first positions, wherein the second parts 660, 662 are fully retracted into the bores 694, 696 of the first parts 654, 656, so that the second parts 660, 662 are fully disposed on a proximal side of the distal ends 700, 701 and the openings 698, 699, the second parts 660 being fully disposed within one of: the first parts 654, 656, the members 628, 630, or a combination of the first parts 654, 656 and the members 628, 630.

In FIG. 7B, the first and second end pieces 644, 646 are illustrated in second positions, wherein the second parts 660, 662 extend distally from the openings 698, 699 of the first parts 654, 656. In the second positions, the second parts 660, 662 are partially located on distal sides of the openings 698, 699 and the distal ends 700, 701 of the first parts 654, 656, the second parts 660, 662 also being located partially on proximal sides of the openings 698, 699 and the distal ends 700, 701 of the first parts 654, 656. Thus, the second parts 660, 662 are partially located in the bores 694, 696 in the second positions.

The second parts 660, 662 of the end pieces 644, 646 are axially movable with respect to the first and second members 628, 630. Each second part 660, 662 may be axially moved to put the end pieces 644, 646 into their first positions (shown in FIG. 7A) and their second positions (shown in FIG. 7B). In the example of FIGS. 7A-7B, the second parts 660, 662 of the first and second end pieces 644, 646 are axially movable between their first and second positions without being detached from the first and second members 628, 630, respectively.

As in the examples of FIGS. 1A-6B, one or more of the end pieces 644, 646 could be provided as an electrode. For example, both of the first and second end pieces 644, 646 may serve electrodes that are configured to apply a current to a tissue when energized. The first and second end pieces 644, 646 may be active bipolar electrodes that are configured to be coupled with and energized by an electrode energy source. In the illustrated example, the current may be provided through lead ends (such as lead ends 24, 26 shown in FIGS. 1A-1B) to each of the end pieces 644, 646.

In some examples, either the first parts 654, 656 or second parts 660, 662 may be energizable as the electrode, and the other first parts 654, 656 or second parts 660, 662 may be an insulated or non-energized part. For example, the first parts 654, 656 could be insulated like the first and second members 628, 630 and the second parts 660, 662 could be provided as energizable electrodes.

An operator may desire to move the second parts 662, 662 out of the first parts 654, 656 of the end pieces 644, 646 if the operator desires to use a narrower part of the end pieces 644, 646. Similarly, the operator may retract the second parts 660, 662 into the first parts 654, 656 if the operator desires wider ends of the forceps 620. In the example where only the second parts 660, 662 are energizable electrodes, the operator may move the end pieces 644, 646 into their second positions if the operator desires to use the electrodes, and the operator may move the end piece into their first positions, wherein the second parts 660, 662 are fully retracted into the first parts 654, 656, when the operator desires to use the forceps 420 as a non-energized gripper or tweezers.

Like the various examples described above, the first and second parts 654, 656, 660, 662 may have various characteristics that have been hereinbefore described. For example, one of the first and second parts 654, 656, 660, 662 may be sharper than the other or have a larger surface area, by way of example.

Similarly, any of the movable forceps 20, 120, 220, 320, 420, 520, 620 described herein, or other configurations, could also have other variations between the first and second parts or sides.

For example, the first parts or sides could have a first coating disposed thereon, and a second parts or sides could have either no coating, or a second coating disposed thereon. In some examples, the first coating could be different than the second coating. Thus, the operator may desire to move the end pieces between the first and second positions to use the sides with either the first coating, no coating, or the second coating.

In another example, a first portion of the first end piece could have a first end piece first thermal capability, and a second portion of the first end piece could have a first end piece second thermal capability, wherein the first end piece first and second thermal capabilities are non-identical. The thermal capabilities could include conductivity, specific heat, heating upon application of power (related to electrical resistance), and/or thermal capacitance, by way of example. Likewise, a first portion of the second end piece could have a second end piece first thermal capability, and a second portion of the second end piece could have a second end piece second thermal capability, wherein the second end piece first and second thermal capabilities are non-identical. These thermal capabilities could differ from each other, such that the operator could move the end pieces between their first and second positions to use a part of the end piece having the desired thermal capability.

In yet another example, a first portion of the first end piece could have a first end piece first electrical capability, and a second portion of the first end piece could have a first end piece second electrical capability, wherein the first end piece first and second electrical capabilities are non-identical—differing from each other. The electrical capabilities could include, for example, resistance and/or current density (conduction contact area). Likewise, a first portion of the second end piece could have a second end piece first electrical capability, and a second portion of the second end piece could have a second end piece second electrical capability, wherein the second end piece first and second electrical capabilities are non-identical. These electrical capabilities could differ from each other, such that the operator could move the end pieces between their first and second positions to use a part of the end piece having the desired electrical capability.

Instill another example, a first portion of the first end piece could have a first end piece first electrical polarity, and a second portion of the first end piece could have a first end piece second electrical polarity, particularly when the end pieces are electrodes or have electrodes. The first end piece first and second electrical polarities are non-identical—differing from each other. The electrical polarities could include energy passage, by way of example. Likewise, a first portion of the second end piece could have a second end piece first electrical polarity, and a second portion of the second end piece could have a second end piece second electrical polarity, wherein the second end piece first and second electrical polarities are non-identical. These electrical polarities could differ from each other, such that the operator could move the end pieces between their first and second positions to use a part of the end piece having the desired electrical polarity.

In still another example, the first portions of the end pieces may be formed of a first material, and the second portions may be formed of a second material that is different than the first material. In some variations, one of the materials is conductive, while the other is insulating.

Figure 8:
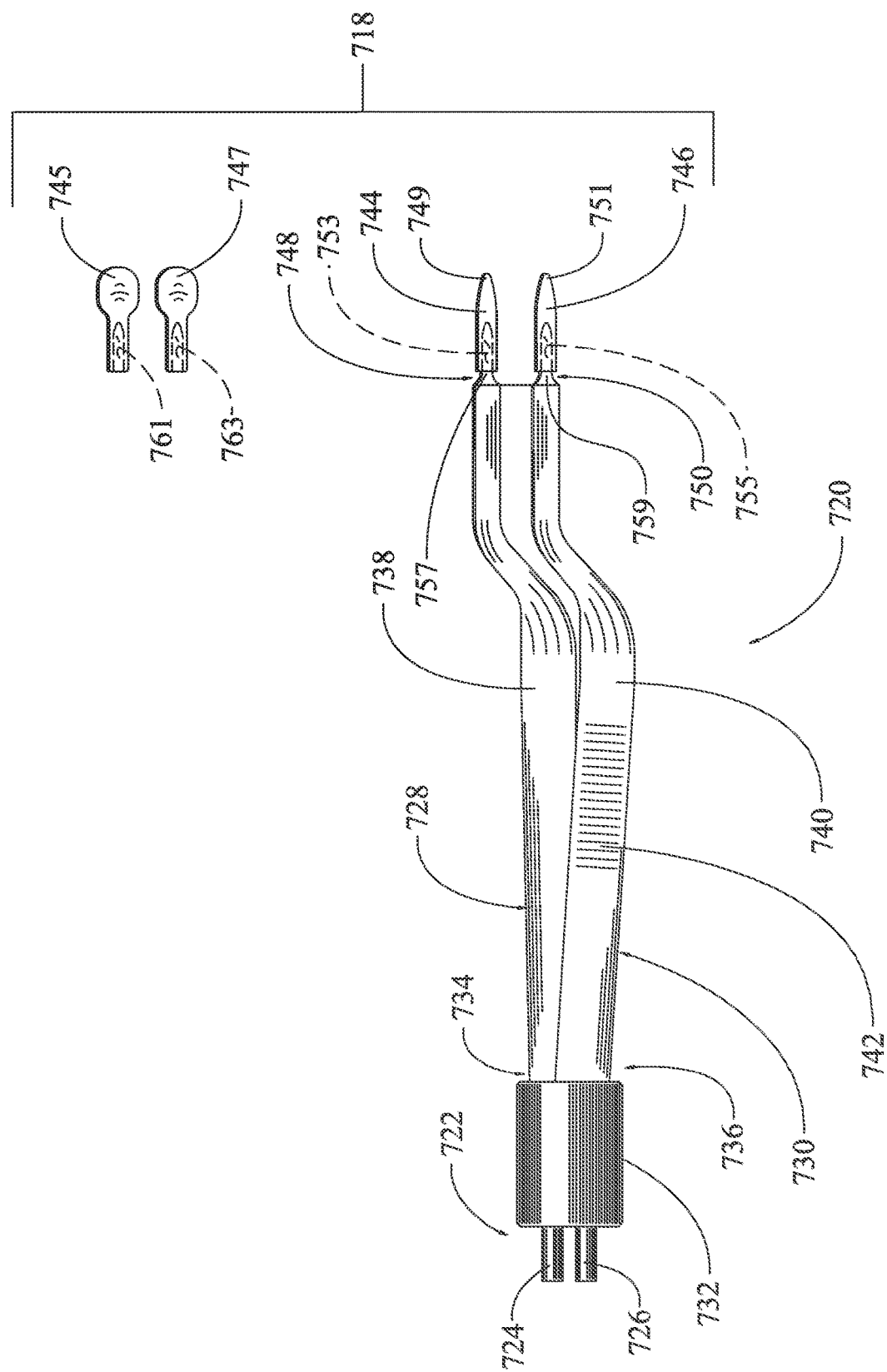
FIG. 8 is a side perspective view of a surgical device kit having interchangeable device ends, in accordance with the principles of the present disclosure.

Referring now to FIG. 8, a portion of an electrosurgical device kit is illustrated and generally designated at 718. The kit 718 includes a surgical forceps 720 and at least two different attachable and detachable end pieces 744, 745.

The surgical forceps 720 may be of the electrosurgical type or the non-energized type, by way of example. For example, if of the non-energized type, the forceps 720 are used for gripping and no energy is applied through the forceps 720. However, if the forceps 720 are of the electrosurgical type, they may be used as a bipolar device, for example, to apply pulsed or non-pulsed energy to coagulate a tissue.

For the forceps 720 of the electrosurgical type, the forceps 720 include a proximal end 722 that may be connected to an energy source via first and second leads 724, 726. The forceps 720 may include a first elongate member 728 and a second elongate member 730, which are connected together at the proximal end 722 of the forceps device 720. The first member 728 is disposed adjacent to the second member 730. In this example, a band 732 surrounds proximal ends 734, 736 of the first and second members 728, 730 to couple the proximal ends 734, 736 together. Thus, the proximal ends 734, 736 may be fixed together by the band 732 as shown. In this example, the first and second members 728, 730 are movably coupled together. As described with respect to FIGS. 1A-1B, the first and second members 728, 730 may be moved toward each other by exerting pressure on their outer sides 738, 740; for example, an operator can pinch the first and second members 728, 730 together and toward each other by gripping and exerting pressure on gripping sections 742 disposed on the outer sides 738, 740. (Though not shown, it should be understood that an identical gripping section 742 is disposed on the outer side 740, as shown on the outer side 738.)

The band 732 and the first and second members 728, 730 may be formed of an insulating material, such as a plastic or rubber. In other configurations, the first and second members 728, 730 may each have an inner portion formed of a conductive material, such as a metal, and an outer casing formed of an insulating material, where the outer casing surrounds the inner portion. In still other configurations, such as non-electrosurgical devices, the first and second members 728, 730 may be formed entirely of a conductive material, such as a metal, by way of example.

The first end piece 744 may be temporarily or removably attached to the distal end 748 of the first member 728. The second member 730 may have a similar second end piece 746 that is removably attached to the distal end 750 of the second member 730. In the alternative, the second member 730 may not have a separate end piece 746; instead, the second member 730 may have a fixed end that is not interchangeable. The end pieces 744, 746 may be identical to each other, as shown, or the end pieces 744, 746 may be different from each other. The end pieces 744, 746 may take on various configurations, which will be described below.

In the illustrated example of FIG. 8, each end piece 744, 746 has an arrow-like shape with a pointed end 749, 751. The ends pieces 744, 746 form a cavity 753, 755 for attaching the end pieces 744, 746 to projections 757, 759 extending from the distal ends 748, 750 of the first and second members 728, 730.

The first type of end pieces 744, 746 may be detached from the first and second members 728, 730, and the second type of end pieces 745, 747 may be attached. Thus, the end pieces 745, 747 are also removably attachable to the first and second members 728, 730. The second type of end piece 745, 747, in this example, is a rounded, blunt end piece 745, 747. Each of the rounded end pieces 745, 747 also form a cavity 761, 763 therein for attaching the rounded end pieces 745, 747 to the projections 757, 759 of the first and second members 728, 730. In the illustrated example, the first type of end pieces 744, 746 are sharper than the second type of end pieces 745, 747. Thus, an operator can use whichever type of end pieces 744, 746, 745, 747 is more suitable for the particular task at hand and attach the desired end pieces 744, 746, 745, 747 to the first and/or second members 728, 730.

In some variations, one or more of the end pieces 744, 746, 745, 747 is an electrode head. For example, both of the types of end pieces 744, 746, 745, 747 may serve as electrode heads for the forceps device 720. The electrode heads 744, 746, 745, 747 are configured to apply a current to a tissue when connected to one of the first and second members 728, 739 and energized. The end pieces 744, 746, 745, 747 may be active bipolar electrodes that are configured to be coupled with and energized by an electrode energy source when attached to one of the first and second members 728, 730. In the illustrated example, the current may be provided through the lead ends 724, 726 to whichever of the end pieces 744, 746, 745, 747 is attached.

Additional interchangeable electrode heads or end pieces may also be provided. For example, referring to FIG. 9A, a set of toothed end pieces 844, 846 (which may be electrode heads, as described above) are provided. Each of the toothed end pieces 844, 846 has a set of teeth 864, 866 for gripping a tissue. Furthermore, referring to FIG. 9B, another set of toothed end pieces 845, 847 (which may be electrode heads, as described above) are provided. The toothed end pieces 845, 847 also have sets of teeth 872, 874. However, the sets of teeth 872, 874 on the end pieces 845, 847 in FIG. 9B have much larger teeth than the sets of teeth 864, 866 of the end pieces 844, 846 shown in FIG. 9A.

As with the forceps 20, 120, 220, 320, 420, 520, 620 described above, the forceps 720 and end pieces 744, 745, 746, 747, 844, 845, 846, 847 may also be provided with various shapes, and having differing materials, coatings, polarities, electrical capabilities, and thermal capabilities.

When used as an electrosurgical device, the forceps 20, 120, 220, 320, 420, 520, 620, 720 is configured to emit an electric signal for ablation, coagulation, or other treatment of nearby tissue. The forceps 20, 120, 220, 320, 420, 520, 620 720 may be of the bipolar type, wherein current is passed through one of the end pieces, through the patient's tissue, and received through the other end piece. In some examples, both end pieces are energized electrodes, which are energized with opposite polarity. For example, a first source signal may be delivered from the first end piece electrode, and a second source signal may be delivered from the second end piece electrode. Each of the first and second signals travel through tissue and return to the other of the two electrodes—the one that did not generate the signal. The electrons flow in a single direction at a time. As the signals oscillate between each electrode, the electrons race toward whichever electrode has a more positive terminal.

The description of the invention is merely exemplary in nature and variations that do not depart from the gist of the invention are intended to be within the scope of the invention. Such variations are not to be regarded as a departure from the spirit and scope of the invention. For example, variations in the various figures can be combined with each without departing from the spirit and scope of the present disclosure.

The preferred embodiment of the present invention has been disclosed. A person of ordinary skill in the art would realize, however, that certain modifications would come within the teachings of this invention. Therefore, the following claims should be studied to determine the true scope and content of the invention.

Any numerical values recited in the above application include ail values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints, the use of "about" or "approximately" in connection with a range apply to both ends of the range. Thus, "about 20 to 30" is intended to cover "about 20 to about 30", inclusive of at least the specified endpoints.

The disclosures of all articles and references, including patent applications and publications, are incorporated by reference for all purposes.

The term "consisting essentially of" to describe a combination shall include the elements, ingredients, components or steps identified, and such other elements ingredients, components or steps that do not materially affect the basic and novel characteristics of the combination.

The use of the terms "comprising" or "including" describing combinations of elements, ingredients, components or steps herein also contemplates embodiments that consist essentially of the elements, ingredients, components or steps.

What is claimed is:

1. A device, comprising:
   an elongate first member;
   an elongate second member disposed adjacent to the elongate first member, the elongate second member movably coupled to the elongate first member;
   wherein a central axis extends from a distal end portion of the device to a proximal end portion of the device and between the elongate first member and the elongate second member; and
   a forceps end coupled to the elongate first member, at least a portion of the forceps end being movable with respect to the elongate first member into a forceps end first position and a forceps end second position, the forceps end having a first face surface and a second face surface and a perimeter edge extending around each of the first face surface and the second face surface;
   wherein at least one of the first face surface or the second face surface face the central axis;
   wherein the first face surface includes a first set of teeth extending towards the central axis from the first face surface within the perimeter edge of the first face surface and the second face surface includes a second set of teeth extending from the second face surface;
   wherein the elongate first member and the elongate second member are configured to have a separated position, and a first gripping position, and a second gripping position;
   wherein in the first gripping position the first set of teeth is disposed closer to the central axis than the second set of teeth, and in the second gripping position the second set of teeth is disposed closer to the central axis than the first set of teeth.

2. The device of claim 1, wherein the first set of teeth is non-identical to the second set of teeth.

3. The device of claim 1, wherein the forceps end is movable between the forceps end first position and the forceps end second position without being detached from the elongate first member.

4. The device of claim 1, wherein the forceps end is rotatably attached to the elongate first member.

5. The device of claim 1, wherein the device includes a first device distal end and a second device distal end, the first set of teeth forming the first device distal end when the forceps end is in the forceps end first position, and the second set of teeth forming the second device distal end when the forceps end is in the forceps end second position.

6. The device of claim 5, wherein in the forceps end first position, the second set of teeth is disposed closer to the device proximal end portion than the first set of teeth is disposed with respect to the device proximal end portion.

7. The device of claim 1, wherein the device is an electrosurgical device, the device includes:
   a second forceps end coupled to the elongate second member, at least a portion of the second forceps end being movable with respect to the elongate second member into a second forceps end first position and a second forceps end second position, the second forceps end having a third forceps portion and a fourth forceps portion, the third forceps portion having a third set of teeth and the fourth portion having a fourth set of teeth.

8. The device of claim 1, wherein a second forceps end coupled to the elongate second member includes a third face surface and a fourth face surface;
   wherein the first face surface is identical to the second face surface and the third face surface is identical to the fourth face surface.

9. The device of claim 8, wherein the first face surface is movable between the first forceps end first position and the first forceps end second position without being detached from the elongate first member, and wherein the third face surface is movable with respect to the elongate second member between a second forceps end third position and a second forceps end fourth position where the third face surface is closer to the central axis than the fourth face surface without being detached from the elongate second member.

10. The device of claim 8, wherein in the first forceps end first position, the second face surface of the first forceps end is disposed closer to the device proximal end portion than the first face surface, and wherein in a second forceps end third position, the third face surface is disposed closer to the device proximal end portion than the fourth face surface.

11. The device of claim 8, wherein in the first forceps end first position, the first face surface is disposed closer to the central axis of the device than the second face surface, and in a second forceps end third position, the third face surface is disposed closer to the central axis of the device than the fourth face surface.

12. The device of claim 1, wherein a second forceps end coupled to the elongate second member includes a third face surface and a fourth face surface, the third face surface includes a third set of teeth and the fourth face surface includes a fourth set of teeth;
   wherein the first set of teeth of the first forceps end forms a first device distal end when the first forceps end is in the first forceps end first position, and the second set of teeth of the first forceps end forms the first device distal end when the first forceps end is in the first forceps end second position, and wherein the third set of teeth of the second forceps end and forms a second device distal end when the second forceps end is in a second forceps end third position, and the fourth set of teeth of the second forceps end forms the second device distal end when the second forceps end is in a second forceps end fourth position.

13. A device, comprising:
an elongate first member;
an elongate second member disposed adjacent to the elongate first member, the elongate second member being at least movably coupled to the elongate first member;
wherein the elongate first member and the elongate second member are configured to be movable between a separated position and a gripping position;
a first forceps end coupled to the elongate first member, at least a portion of the first forceps end being movable with respect to the elongate first member into a first forceps end first position and a first forceps end second position, the first forceps end having a first face surface and a second face surface, the first face surface having a first set of teeth and the second face surface having a second set of teeth;
wherein at least one of first set of teeth or the second set of teeth extend toward a central axis of the device in the first forceps end first position; and
a second forceps end coupled to the elongate second member, at least a portion of the second forceps end being movable with respect to the elongate second member into a second forceps end third position and a second forceps end fourth position, the second forceps end having a third face surface and a fourth face surface, the third face surface having a third set of teeth and the fourth face surface having a fourth set of teeth;
wherein at least one of the third set of teeth or the fourth set of teeth extend toward the central axis of the device in the second forceps end third position;
wherein in a first gripping position of the gripping position, the first set of teeth and the third set of teeth are positioned closer to the central axis than the second set of teeth and the fourth set of teeth, and in a second gripping position of the gripping position, the second set of teeth and fourth set of teeth are positioned closer to the central axis than the first set of teeth and the third set of teeth.

14. The device of claim 13, wherein the first forceps end and the second forceps end are identical.

15. The device of claim 13, wherein the first set of teeth of the first and the second set of teeth are non-identical to the third set of teeth and the fourth set of teeth.

16. The device of claim 13, wherein the first forceps end is rotatably attached to the elongate first member and the second forceps end is rotatably attached to the elongate second member;
wherein one or more of the first forceps end and the second forceps end are electrodes that are configured to apply a current to a tissue when energized.

* * * * *